United States Patent [19]

Iijima et al.

[11] Patent Number: 5,724,252

[45] Date of Patent: Mar. 3, 1998

[54] SYSTEM FOR PREDICTION OF PROTEIN SIDE-CHAIN CONFORMATION AND METHOD USING SAME

[76] Inventors: Hiroshi Iijima, c/o Kirin Beer Kabushiki Kaisha Kiban Gijutsu Kenkyusho, 1-13-5, Fukuura, Kanazawa-ku, Yokohama-shi, Kanagawa-ken; Yusuke Naito, Bay-city Urayasu I-105, 6-Hinode, Urayasu-shi, Chiba-ken, both of Japan

[21] Appl. No.: 352,621

[22] Filed: Dec. 9, 1994

[51] Int. Cl.$^6$ .................. G06F 17/159; G01N 33/00; G01N 37/00

[52] U.S. Cl. .................................... 364/496; 364/578

[58] Field of Search .................... 364/496, 578; 435/69.1

[56] References Cited

U.S. PATENT DOCUMENTS 5,526,281  6/1996  Chapman et al. .............. 364/496
5,553,004  9/1996  Gronbech-Jensen et al. ...... 364/496

OTHER PUBLICATIONS

J. Mol. Biol., 1991, vol. 217, pp. 373–388, Christopher Lee, et al., "Prediction of Protein Side–Chain Conformation by Packing Optimization".

Proteins: Structure, Function, and Genetics, vol. 2, pp. 330–339, 1987, Hiroshi Iijima, et al., "Calibration of Effective Van Der Waals Atomic Contact Radii for Proteins and Peptides".

Journal of Computational Chemistry, vol. 5, No. 2, pp. 129–145, 1984, U. Chandra Singh, et al., "An Approach to Computing Electrostatic Charges for Molecules".

Journal of Computational Chemistry, vol. 10, No. 8, pp. 982–1012, Matthew Clark, et al., "Validation of the General Purpose Tripos 5.2 Force Field".

Proceedings of The first IEEE Conference on Evolutionary Computation, Jun. 1994, vol. 1, Hiroshi Iijima, et al., "Incremental Prediction of the Side–Chain Conformation of Proteins by a Genetic Algorithm", pp. 362–367.

*Primary Examiner*—Edward R. Cosimano

[57] ABSTRACT

In the prediction of side-chain conformation of protein, conformations are predicted by describing a candidate conformation in the form of an array whose components are the torsion angles of a side chain, subjecting a plurality of solution candidates to evaluation, increasing side chains in a stepwise manner, judging the appropriateness of a solution candidate based upon degree of its van der Waals contact, and generating a new solution candidate by changing torsion angle to an arbitrary value or by interchanging the components of the torsion-angle arrays of two solution candidates. Further, the foregoing processing is executed with respect to the main-chain conformation whenever a side-chain conformation corresponding to one amino acid residue is constructed, and construction of all side-chain conformations is performed in incremental fashion.

8 Claims, 6 Drawing Sheets

| $x^1$ | $x^2$ | $x^3$ | $x^4$ | $x^1$ | $x^2$ | $x^1$ | $x^2$ | $x^1$ | $x^2$ | --- | $x^1$ |
|---|---|---|---|---|---|---|---|---|---|---|---|
| Arg1 | | | | Asp3 | | Phe4 | | Leu6 | | --- | Thr54 |

FIG. 7A

BOVINE PANCREATIC TRYPSIN INHIBITOR

SYSTEM FOR PREDICTION OF PROTEIN SIDE-CHAIN CONFORMATION AND METHOD USING SAME

BACKGROUND OF THE INVENTION

This invention relates to a system for predicting protein side-chain conformation (conformation represented by three-dimensional coordinates of the atoms constructing the side chain) from the main-chain conformation (conformation represented by three-dimensional coordinates of the atoms constructing the main chain) of protein and an amino acid sequence that have been recorded on a magnetic recording medium of a computer. The invention further relates to a method which makes use of this system.

When the side-chain conformation of protein is predicted from the main-chain structure thereof in the prior art, candidate conformations are generated and evaluated by energy computation using molecular mechanics and/or molecular dynamics. In energy computations based upon molecular mechanics and/or molecular dynamics, a considerably long period of time is required to calculate the interactions between one atom and all other atoms. In some of the methods adopted in the prior art, combinations in which interactions are computed are limited to some of the atoms in order to reduce the amount of calculation. Another expedient is to repeat computations while changing only some the side-chain conformations of solution candidates so as to lower the energy, though accuracy is sacrificed. Regardless of the method, however, the amount of calculation is much higher than that used in the method of predicting protein side-chain conformation in the present invention.

To the best of our knowledge, all of the conventional methods employ techniques through which candidates for side-chain conformation are generated by being selected from a limited number of side-chain conformation rotomer libraries in order to overcome the disadvantage of the prolonged period of time needed for the computation of energy based upon molecular mechanics and/or molecular dynamics. According to methods which depend upon a library, solution candidates are generated from structures of limited type. This is a drawback in that the combinations of side-chain conformations generated are too few in number or type. In other words, the accuracy of the solutions obtained is limited in order to narrow down the range (search space), in which solutions are sought, for the purpose of shortening computation time. A method of generating conformations based upon simulated annealing in order to overcome this narrowness of search space has been proposed. (For example, see C. Lee & S. Subbiah, *J. Mol. Biol.*, vol. 217, 373–388, 1991.) However, in view of the fact that there are cases in which the potential surface of molecular dynamic energy generally is not flat and does not exceed the local minima, the computational computation is very high.

In order to predict side-chain conformations of protein from main-chain structure in the prior art, force field energy such as van der Waals potential energy between the atoms of candidate conformations, the energy of electric charge and hydrogen bonding energy is calculated and the predicted conformations are revised and evaluated using the energy values calculated. The computations require a long period of time for this reason.

In addition, since candidate conformations are selected from a limited group of side-chain conformation candidates put into the form of a library, the prediction of conformations not included in the library is not assured.

Furthermore, only one candidate conformation is given for one act of prediction.

SUMMARY OF THE INVENTION

An object of the present invention is to provide a system for predicting protein side-chain conformation, as well as a method using this system, in which a computational method simpler and finer than the conventional method of energy computation is applied to limited combinations of atoms, thereby shortening computation time and generating solution candidates, without relying upon a library, so as to employ a theoretically unlimited search space, and in which prediction accuracy is improved by making predictions using a plurality of solution candidates.

In order to solve the foregoing object, the present invention provides a system for predicting protein side-chain conformation, as well as a method using this system, according to which conformations are predicted by describing a candidate conformation in the form of an array whose components are the torsion angles of a side chain, subjecting a plurality of solution candidates to evaluation, increasing side chains in stages, judging the appropriateness of a solution candidate based upon degree of its van der Waals contacts, and generating a new solution candidate by changing torsion angle to an arbitrary value or by interchanging the components of the torsion-angle arrays of two solution candidates. Further, the foregoing processing is executed with respect to the main-chain conformation whenever a side-chain conformation corresponding to one amino acid residue is constructed, and construction of all side-chain conformations is performed in incremental fashion. The means for implementing this processing are described below in detail.

At a prediction stage at which one side chain is targeted, values of the torsion angles of this side chain are given individually as random numbers for each of a plurality of solution candidates, and three-dimensional coordinates of the side-chain atoms are computed from the values of these torsion angles using standard bond lengths and bond angles. It is determined whether no other atoms are present within the van der Waals radii of each of the protein atoms. If other atoms are present, then the inter-atomic distance between the two atoms is determined. Different solution candidates are generated until a solution is obtained in which there are no other atoms present within the van der Waals radii of all protein atoms. In the determination regarding whether no other atoms are present within the van der Waals radii of the protein atoms or how close any other atoms are, atom pairs which undergo scrutiny are reduced by storing, in computer memory, in which lattice of three dimensional space the atom positions of each solution candidate exist, wherein three-dimensional space is subdivided into lattices the distance between which is twice the maximum van der Waals radius found among the types of atoms. The generation of different solution candidates is performed by choosing any solution candidate randomly, choosing any torsion angle in the solution candidate randomly and changing the value thereof to an arbitrary value. Alternatively, different solution candidates may be generated by choosing any two solution candidates from a plurality of solution candidates randomly, choosing a part of the components of the torsion-angle arrays of the two solution candidates randomly and interchanging these parts.

As many apparently widely different embodiments of the present invention can be made without departing from the spirit and scope thereof, it is to be understood that the invention is not limited to the specific embodiments thereof except as defined in the appended claims.

DESCRIPTION OF THE PREFERRED EMBODIMENTS

A first embodiment of the present invention will now be described with reference to the accompanying drawings.

Figure 1:
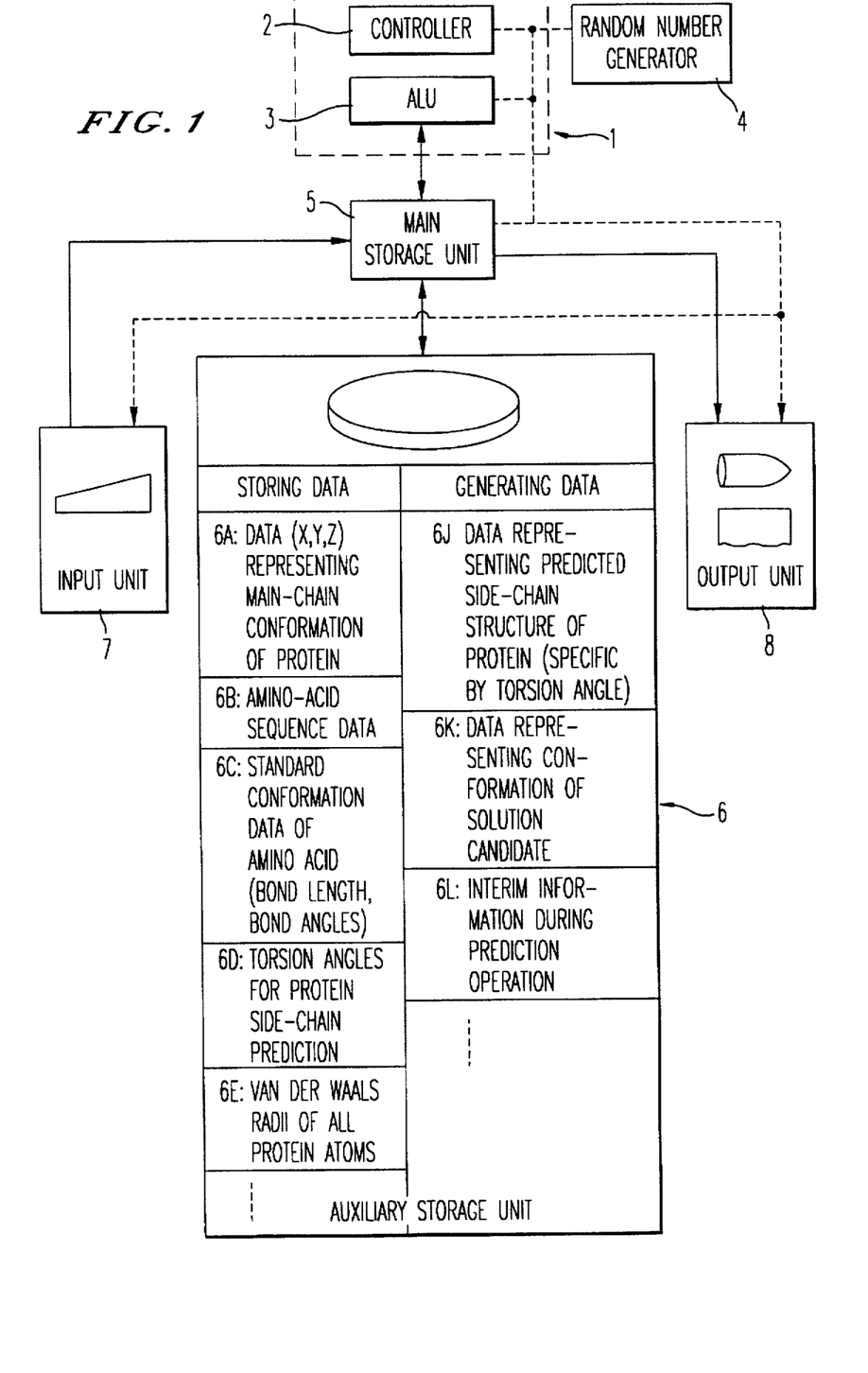
FIG. 1 is a diagram showing the general configuration of a system for predicting protein-side chain conformation according to an embodiment of the present invention.

As shown in FIG. 1, the system according to the invention includes a processor 1 for interpreting and executing instructions. The processor 1 comprises a controller 2, an arithmetic and logic unit (ALU) 3 and a register (not shown). The controller 2 interprets program instructions and carries out overall control of the processor, such as the exchange of signals with various other components. The ALU 3 performs arithmetic and logical operations. The register, which can be considered to be a memory device within the processor, is capable of writing in data simply and at high speed. The system further includes a random-number generator 4 for generating random numbers, and a main storage unit 5, which comprises a ROM for storing programs and a RAM for storing data temporarily. The main storage unit 5 is capable of writing and reading information to and from addresses designated directly by the processor 1. Also provided are an auxiliary storage unit 6, such as a magnetic storage medium, which makes up for any insufficiency in the storage capacity of the main storage unit 5, an input 7 such as a keyboard, and an output 8 such as a display or printer.

By generating random numbers, the random-number generator 4 in this system for predicting protein side-chain conformation according to the invention finds use in selecting combinations of solution candidates to be paired, selecting portions at which crossover occurs, selecting solution candidates which provide mutations, selecting the mutated portions and changing the values of torsion-angle components in a side chain. The details will be described later.

Data stored in the auxiliary storage unit 6 in advance include main-chain conformation data of the protein (three-dimensional atomic coordinates X, Y, Z of the atoms that belong to the chain) 6A; data 6B representing the amino acid sequence; standard structural data (bond lengths and bond angles) 6C of the amino acid; torsion angles (0°–360°) 6D for predicting protein side chains; and van der Waals radii data 6E of all protein atoms. Data that are generated and stored in the auxiliary storage unit 6 include data (specification of a torsion angle by a random number) 6J representing the predicted side-chain conformation of a protein; data 6K representing solution candidates; and interim data 6L generated in the course of a prediction operation.

Figure 2A:
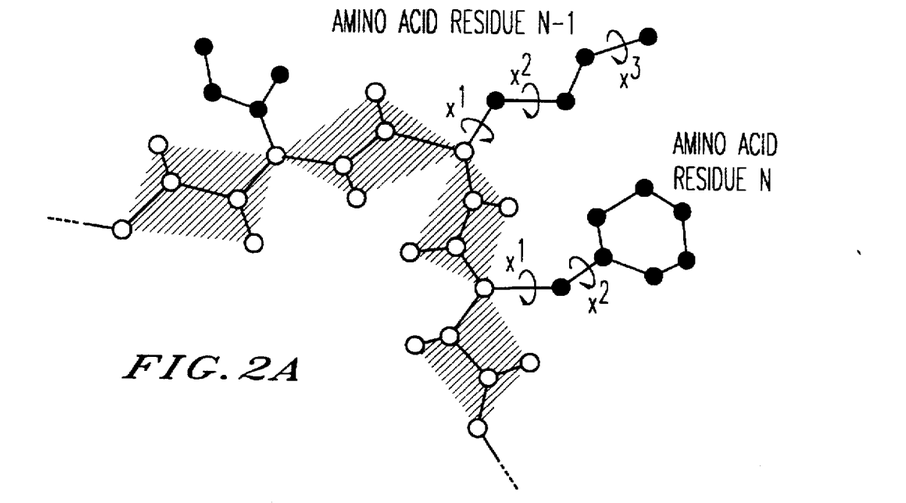
FIG. 2A is an explanatory view illustrating the principle and operation of the system for predicting protein-side chain conformation according to the present invention.

As shown in FIGS. 1 and 2A/2B, the system reads the protein main-chain conformation and the amino acid residue sequence out of the auxiliary storage unit, such as the aforesaid magnetic storage medium, individually provides, for each of a plurality of solution candidates, values of the torsion angles of the side chain in the form of random numbers generated by the random-number generator 4, computes three-dimensional coordinates (X, Y, Z) of the side-chain atoms from the values of the torsion angles using the standard bond lengths and bond angles, determines whether no other atoms are present within the van der Waals radii of each of the protein atoms, or, if other atoms are present within van der Waals radii, determines how close they are, and generates different solution candidates until a solution is obtained in which there are no atoms present within the van der Waals radii off all protein atoms. In the determination regarding whether no other atoms are present within the van der Waals radii of each protein atom or how close any other atoms may be if they are present, atoms subjected to scrutiny are limited by storing in which lattice of three dimensional space the atom positions of each solution candidate exist, wherein three-dimensional space is subdivided into lattices the distance between which is Dm (see FIGS. 4A/4B), namely twice the maximum van der Waals radius found among the types of atoms. The generation of different solution candidates is performed by choosing any solution candidate randomly based upon the random numbers generated by the random-number generator 4, choosing any torsion angle in the solution candidate randomly based upon the random numbers generated by the random-number generator 4, and changing this value to an arbitrary value. Alternatively, different solution candidates may be generated by choosing any two solution candidates from a plurality of solution candidates randomly based upon the random numbers generated by the random-number generator 4, choosing a part of the components of the torsion-angle arrays of the two solution candidates randomly based upon the random numbers generated by the random-number generator 4, and interchanging them. The results obtained by predicting the protein side-chain conformation are written in the auxiliary storage unit 6 such as the magnetic storage medium.

Figure 2B:
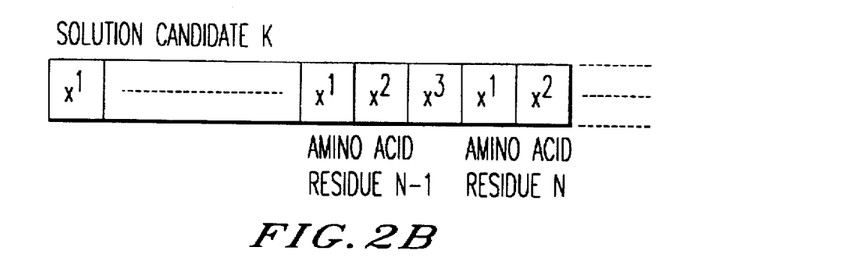
FIG. 2B is a tabular representation of a solution candidate.

FIGS. 2A/2B illustrate a stage at which the side-chain conformation of an amino acid residue, in which one solution candidate (K) is not the final amino acid residue, is predicted. In the state shown in FIGS. 2A/2B, no other atoms exist within the van der Waals radii of individual atoms in a main chain and in a side chain that has been generated thus far. Hereinafter, the value of an M-th torsion angle of a side chain of residue L in the candidate K shall be represented by X(K,L,M). In a side-chain conformation in which X(K,N−1,3) is given from X(K,1,1), the prevailing state is one in which no other atoms exist within the van der Waals radii of all side-chain atoms and all main-chain atoms up to amino acid residue N−1 of the protein. Now assume that the torsion angle X(K,N,2) is given, on the basis of a random number, from the torsion angle X(K,N,1) in the side chain of the amino acid residue N, and that another atom is present within the van der Waals radii of the side-chain atoms of the amino acid residue N. When a random mutation is applied with respect to this solution candidate, an arbitrary side chain of the amino acid residues from 1~N is selected randomly by the random number and this torsion angle is changed to a different value, thereby changing the positions of the atoms in the selected side chain of the amino acid residue. At this time, both the original solution candidate and the solution candidate generated anew by the mutation are saved in memory. Alternatively, when a solution candidate is selected as one which gives crossover in combination with another solution candidate (J), the value of X(K,H,M) from X(K,1,1) of the solution candidate K and the value of X(J,H,M) from the corresponding X(J,1,1) of the solution candidate J are interchanged (crossed), with the boundary being an arbitrary position (H) in the side-chain torsion-angle array of the amino acid residues 1~N. As a result of the interchange of values, the positions of the side-chain atoms of both solution candidates are changed. The solution candidate whose position has been changed and the solution candidate possessing the original side-chain position are both saved in memory.

In order to describe side-chain prediction in an easily understandable manner, the simplest example will be discussed with reference to FIGS. 3A–3C.

Figure 3A:
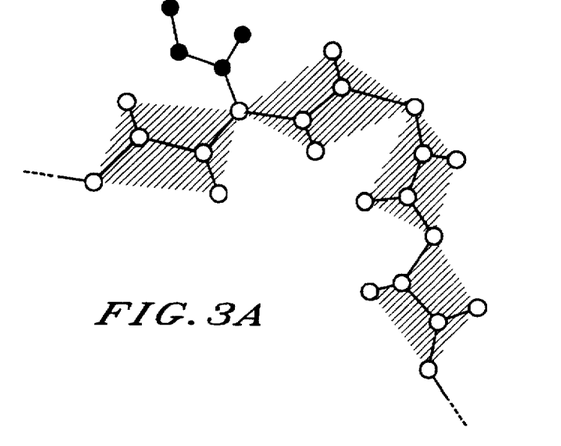
FIGS. 3A, 3B, and 3C are diagrams showing one example of a process for predicting protein-side chain conformation according to the present invention.

(1) FIG. 3A illustrates a state in which no other atoms are present within the van der Waals radii of the individual atoms of a main chain and of a side chain generated thus far.

Figure 3B:
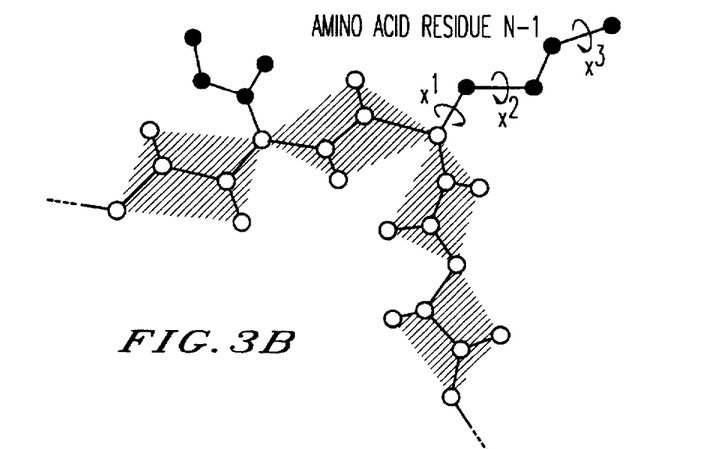

(2) In order to predict a side chain of the amino acid residue N–1 of this protein starting from the illustrated condition, the torsion angles of a side chain of the amino acid residue N–1 are given by random numbers, as shown in FIG. 3B, and a check is made to determine whether no other atoms are present within the van der Waals radii of the individual atoms of this side chain, whereby a side chain of the amino acid residue N–1 is predicted.

Figure 3C:
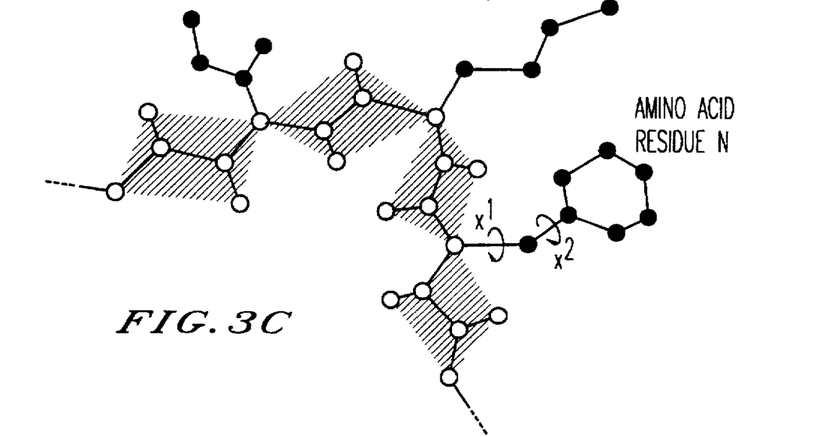

(3) Next, in order to predict a side chain of the amino acid residue N of this protein, as shown in FIG. 3C, the torsion angles of a side chain of the amino acid residue N are given by random numbers in a case where it is assumed that the side chain of the amino acid residue N–1 can be kept fixed, and a check is made to determine whether no other atoms are present within the van der Waals radii of the individual atoms of this side chain, whereby a side chain of the amino acid residue N is predicted.

Naturally, in a case where it is necessary to perform readjustment of the side chain of the amino acid residue N–1 and the side chain of the amino acid residue N or side chains generated thus far, the adjustment is made upon generating the torsion angles of these side chains again by random numbers and checking to determine that there are no other atoms within each other's van der Waals radii.

By means of this operation, a conformation that has undergone mutation and crossover and the original conformation are evaluated, in terms of all main-chain atoms and side-chain atoms up to the amino acid residue N, based upon the extent to which other atoms are present within the van der Waals radii of these atoms, conformations are chosen in order starting from those which exhibit the lowest degree of overlapping of van der Waals radii, and the chosen conformations serve as solution candidates to be scrutinized in the next operation.

Figure 4A:
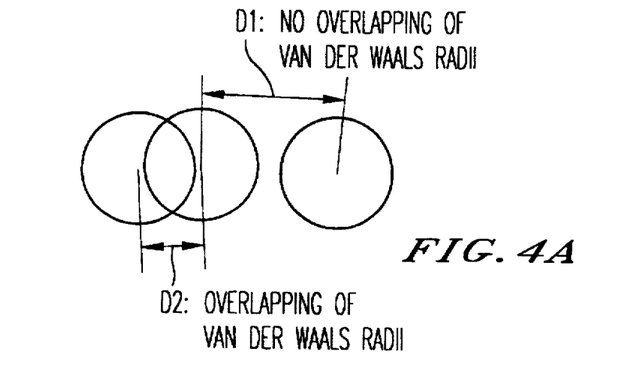
FIG. 4A is a explanatory view of overlapping and no overlapping of van der Waals radii.
Figure 4B:
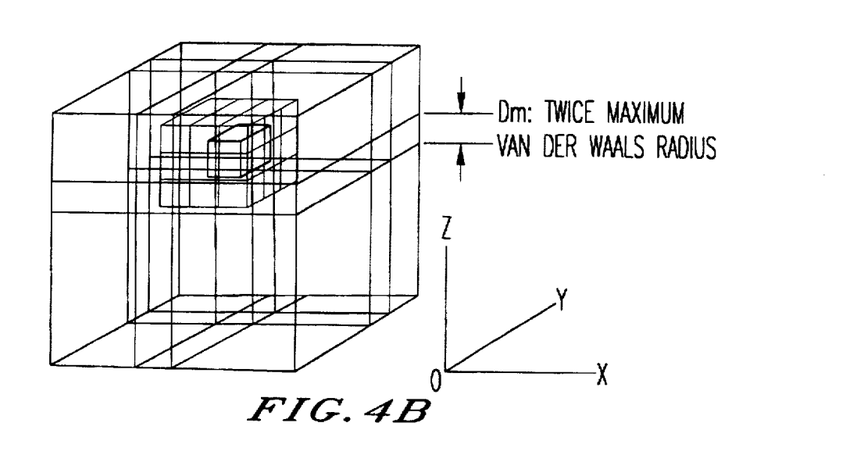
FIG. 4B is an explanatory view showing lattice space in which a search is made for interrelationship between atoms in the prediction of protein-side chain conformation according to the present invention.

As shown in FIGS. 4A/4B, where atoms are present in three-dimensional space divided into the form of lattices is stored in memory. As a result, atoms for which van der Waals contact with a certain atom is deemed possible are limited to an atom present in a three-dimensional lattice in which the above-mentioned atom itself exists, as well as atoms present in 26 three-dimensional lattices neighboring the above-mentioned lattice. The degree of contact (the extent to which atoms overlap each other) can be determined by finding the distance D between the above-mentioned atom and these other atoms in three-dimensional coordinates and calculating the difference between this distance D and the sum $(r_i+r_j)$ of van der Waals radii of the two atoms [i.e., by performing the calculation $(r_i+r_j)-D$]. Here the size of a lattice is made twice the van der Waals radius of the atom having the maximum atomic radius among all of the atoms constructing the protein.

Since the present invention is thus so adapted that position is changed randomly using a plurality of solution candidates, a large number of combinations of side-ring positions can be subjected to evaluation.

Further, in accordance with the present invention, a technique is adopted in which the number of target atoms is reduced in the investigation of van der Waals radii of atom pairs. This makes it possible to shorten computation time.

Figure 5A:
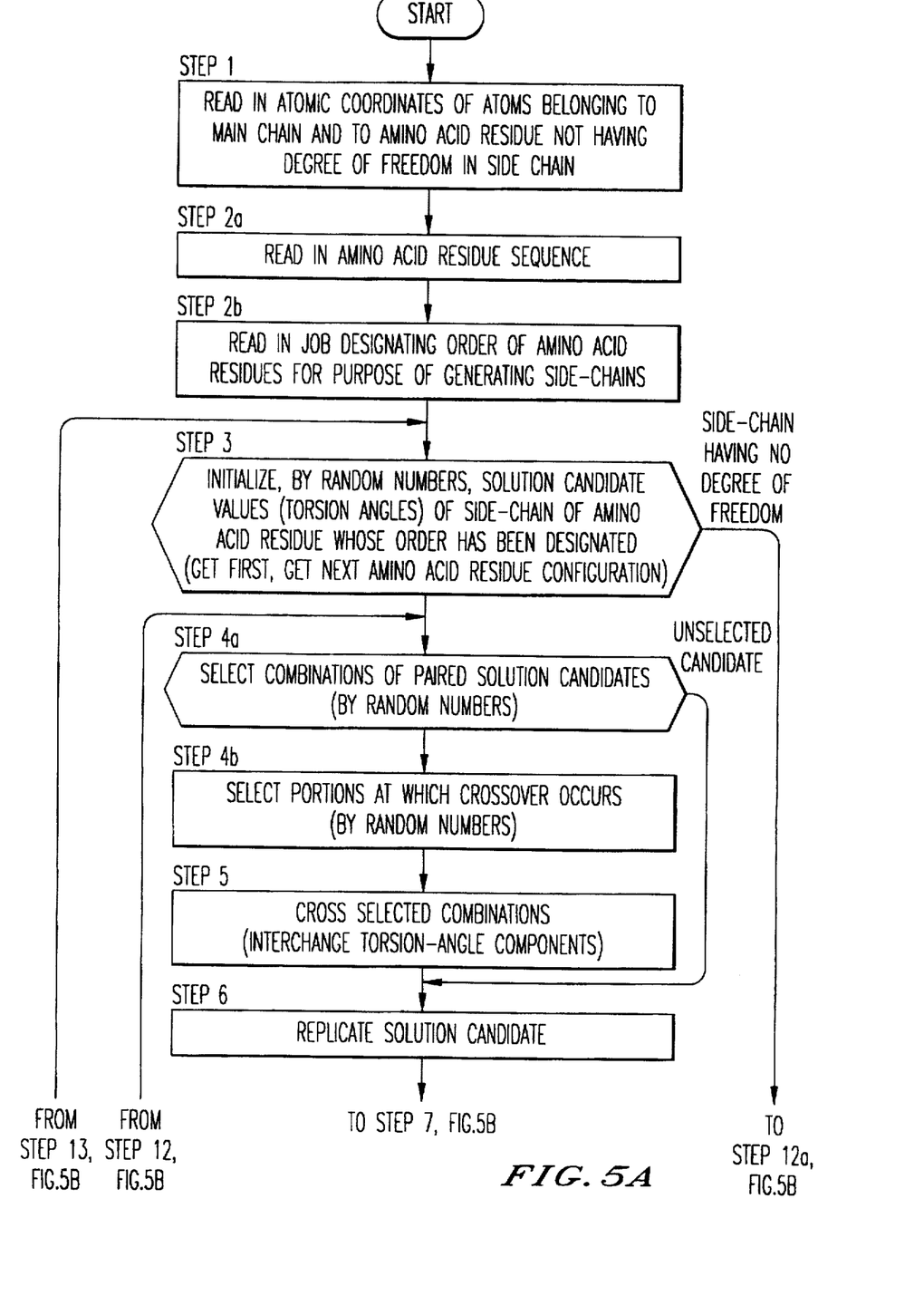
FIGS. 5A/5B is a flowchart illustrating the prediction of protein-side chain conformation according to the present invention.
Figure 5B:
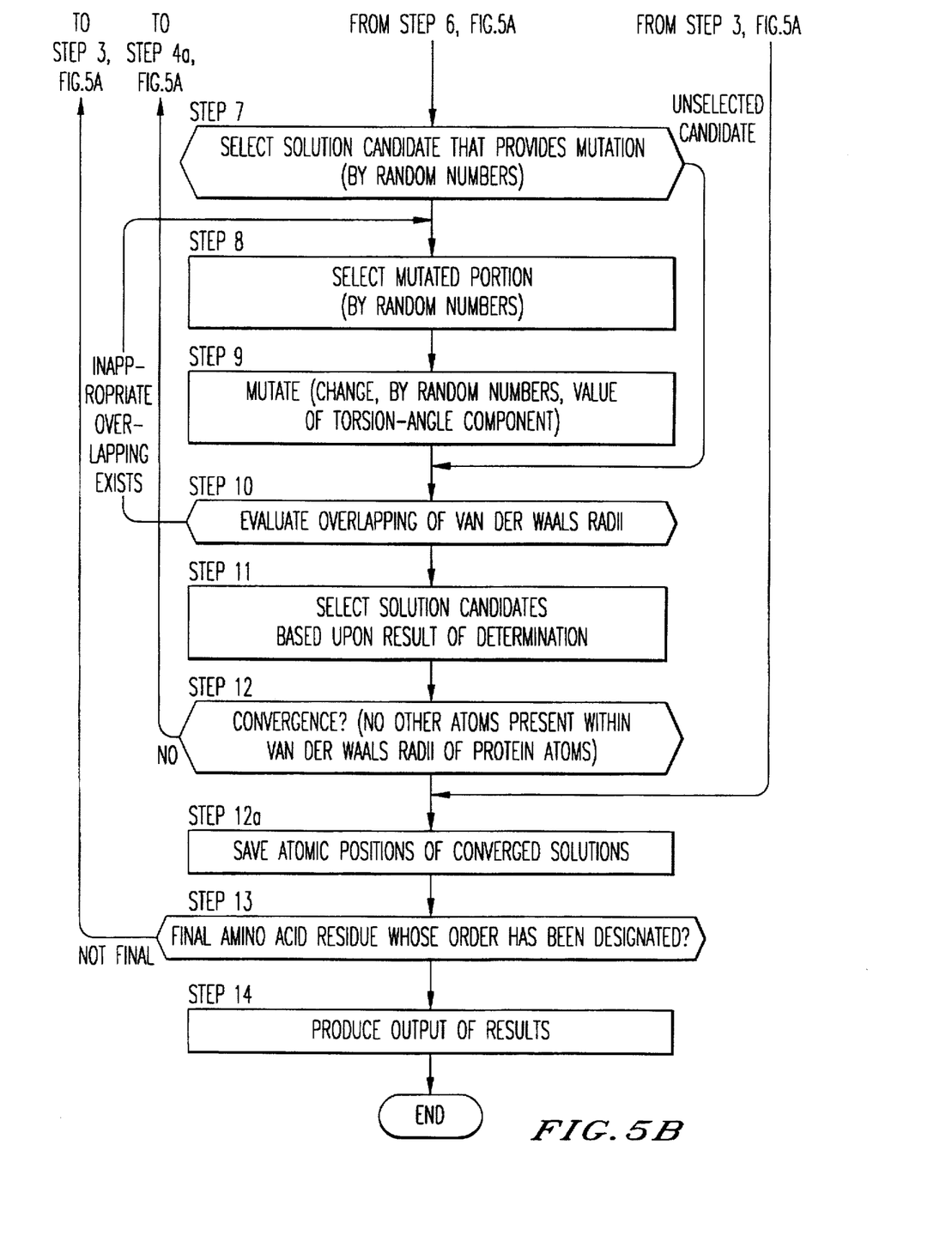

An example of a routine for predicting protein side-chain conformation will now be described with reference to the flowchart of FIGS. 5A/5B.

Figure 6:
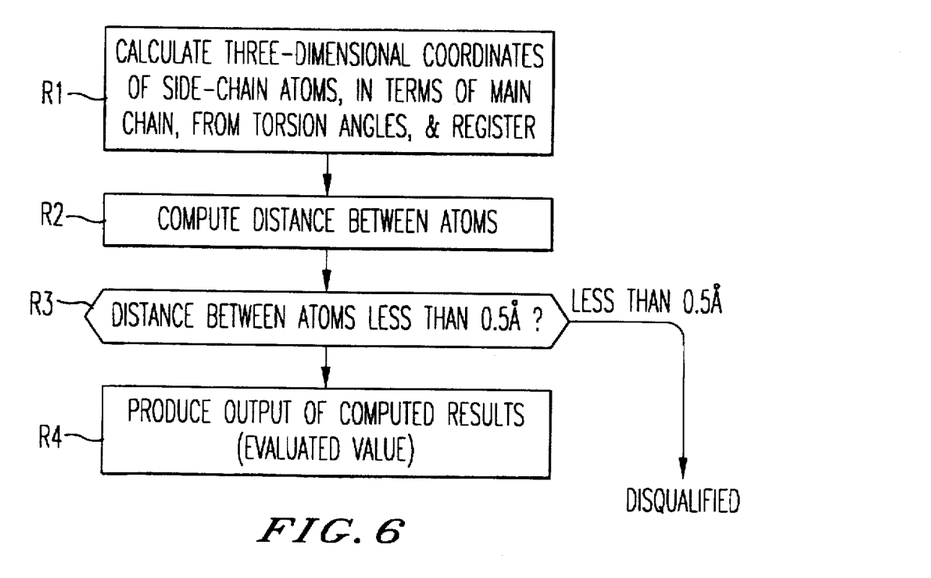
FIG. 6 is a flowchart illustrating evaluation of the degree of overlap of van der Waals radii between atoms in the principle of prediction of protein-side chain conformation according to the present invention.

When the protein main-chain conformation (represented by three-dimensional coordinates of the atoms in the main-chain conformation) and amino acid residue sequence are read and the routine (steps 1 through 14) for predicting protein side-chain conformation is started, the three-dimensional coordinates of the side-chain atoms belonging to the amino acid residue having a side chain which is not free are obtained by calculation and these coordinates are registered together with the entered main-chain conformation (step 1). At this time, to which three-dimensional lattice the atoms belong is stored as registered information representing the atoms. The lattices are subdivided at a size which is twice the radius of the atom having the largest van der Waals radius in the atoms constituting the protein. Next, the amino acid sequence is read in (step 2a), followed by the job designating order of the amino acid residues for the purpose of generating a side chain. In other words, the order of amino acid residues to undergo prediction is read in (step 2b). Next, initial values are set, by random numbers, from values X(1,1,1) to X(L,1,P) of P-number of torsion angles of the side chain of an amino acid residue (I) having the degree of freedom of a side chain designated so as to be processed first (step 3) (if the side chain of amino acid residue (I) has no degree of freedom, processing is completed for that side chain). From L-number of solution candidates generated using an amino acid residue having a degree of freedom in the side chain as the target, paired sets are selected, by random numbers, from all solution candidates at a fixed pairing probability (step 4a) (candidates not selected are provided to step 6 for replication), portions at which crossover occurs are selected by random numbers (step 4b) and crossover is performed at a fixed crossover probability in the selected sets of solution candidates by interchanging the torsion-angle components (step 5). Replication is carried out upon collecting together candidates that have been crossed and candidates that have not been crossed, whereby the number of solution candidates is doubled (i.e., made 2L in number) (step 6). After replication, a candidate (1) which provides a mutation is selected at a fixed mutation probability by random numbers (step 7) (candidates not selected are provided to step 10 for van der Waals evaluation), a torsion-angle component (1,m,n) that provides a mutation is selected arbitrarily from this candidate by random numbers (step 8), and the torsion angle is given by random numbers (step 9). In other words, a mutation due to a random-number change in the value of a torsion-angle component is applied. Candidates which have given a mutation, candidates which have not given a mutation and candidates maintaining the values which prevailed prior to replication are all collected together and it is determined whether no other atoms are present within the van der Waals radii of each of the protein atoms in the conformation indicated by the value of the pertinent solution candidate. If other atoms are present within the van der Waals radii, then how close they are is determined (step 10). To execute this determination, a determination routine (FIG. 6; steps R1–R4) is called at step 10 (if atoms within the van der Waals radii are distanced by less than 0.5 Å, the side chain is disqualified). In the determination, an atom which is the target of evaluation is subjected to evaluation based upon van der Waals contact between atoms. This is carried out by computation, indicated by Equation (1) below, using the processor 1. To accomplish this, first the positions of the side-chain atoms are calculated from the values of the torsion angles of the solution, and the positions are registered (step R1). At this time, through an operation similar to that for the case in which the coordinates of the main chain and the like were read in (step 1 above), to which space the atoms belong is stored as registered information representing the atoms. The space is subdivided by lattices having a size Dm (see FIGS. 4A/4B), which is twice the maximum van der Waals radius of the type of atom serving as the target. Atoms whose van der Waals radii overlap atoms of interest taken in order starting from the atoms of the main chain are retrieved from the registered information and distance between the atoms is computed (step R2). If there is atomic contact in which the distance between atoms is less than a given value (0.5 Å), this solution candidate serving as the target is immediately judged to be unsuitable (step R3). In this case, a solution candidate having a different value is generated at step 10 by mutating the torsion angles of the side chain. If the side-chain conformation is found to be suitable at step R3, then values obtained by multiplying the difference between the sum of the radii and the distance between atoms by M are totaled with regard to the atoms whose van der Waals radii overlap, the total value is raised to the 1/M-th power and the outcome is adopted as the result of the determination.

$$\text{Evaluated value} = \left\{ \sum_{\text{All Atoms}} \text{overlap}(i,j)^M \right\}^{1/M} \quad \text{Eq. (1)}$$

$$\text{Overlap}(i,j) = \begin{array}{ll} 0 \ldots & r_i + r_j \leq d(i,j) \\ (r_i + r_j) - d(i,j) \ldots & r_i + r_j > d(i,j) \end{array}$$

where $r_i$, $r_j$ represent the van der Waals radii of atom i and atom j, respectively, and $d(i,j)$ represents the distance between these two atoms. The results of the computations in steps R1, R2 and R3 are produced as output (step R4).

Depending upon the value obtained as the result of evaluating the solution candidates, half the number (L, which is the same as the number prior to replication) of solution candidates is selected in order starting from the smaller values (step 11). If a solution exists in which there are no other atoms present within the van der Waals radii of each of the atoms of the protein, then computation with regard to the side chain of this amino acid residue is terminated (step 12) and processing returns to step 3 for the side chain of the next amino acid residue (step 13). However, in a case where another atom is present within the van der Waals radii of the protein atoms irrespective of the solution, processing returns to step 4a so that the computations are repeated from the crossover. All atomic positions of a solution in which there are no other atoms present within the van der Waals radii of the protein atoms are written in the auxiliary storage unit 6 such as the magnetic medium. The results of the above computations are produced as output (step 14).

A second embodiment of the present invention will now be described with reference to FIGS. 7A/7B.

It should be noted that the parameters illustrated in this embodiment represent only one example and do not limit the scope of the claims.

Only the coordinates of the main-chain atoms were recorded on a magnetic storage medium from coordinate data (registration code 4PTI) representing the protein molecules of bovine pancreatic trypsin inhibitor, obtained from the "Protein Data Bank" of Brookhaven National Laboratories, acquired by high-resolution X-ray analysis of the crystal structure. In this example, the set-up was such that side chains were generated in the order of the amino acid sequence from the amino end to the carboxyl end.

In the protein molecules of the bovine pancreatic trypsin inhibitor, the positions of the side-chain atoms can be determined if the main-chain conformation has been established for the following amino acid residues, in which there is no degree of freedom in the side chain: Pro2, Cys5, Pro8, Pro9, Gly12, Pro13, Cys14, Ala16, Ala25, Ala27, Gly28, Cys30, Gly36, Gly37, Cys38, Ala40, Ala48, Cys51, Gly56, Gly57 and Ala58. At this time, the side-chain atomic positions are generated by computation from the torsion angles of each side chain using standard bond lengths and bond angles as obtained by X-ray structural analysis (H. Iijima, J. B. Dunbar and G. R. Marshall, 1987, *Proteins: Structure, Function and Genetics*, vol. 2, 330–339) or standard bond lengths and bond angles as determined in an AMBER force field (U. Chandra Singh and Peter A. Kollman, 1984, *Journal of Computational Chemistry*, vol. 15, No. 2, 129–145) or in a Tripos force field (M. Clark, R. D. Cramer III and Nicole Van Opdenbosch, 1989, *Journal of Computational Chemistry*, vol. 110, 982–1012), etc. In the case of protein molecules of the bovine pancreatic trypsin inhibitor, a side chain of 38 amino acid residues is obtained.

Figure 7A:
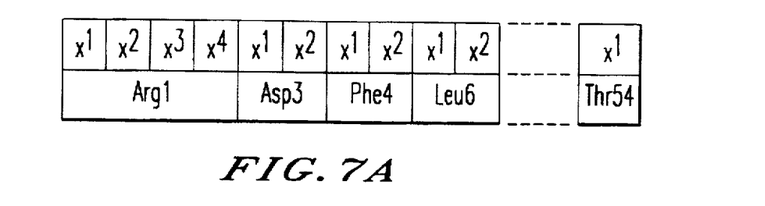
FIG. 7B is an explanatory view showing the particulars of a candidate for side-chain conformation in a second embodiment of the present invention.
Figure 7B:
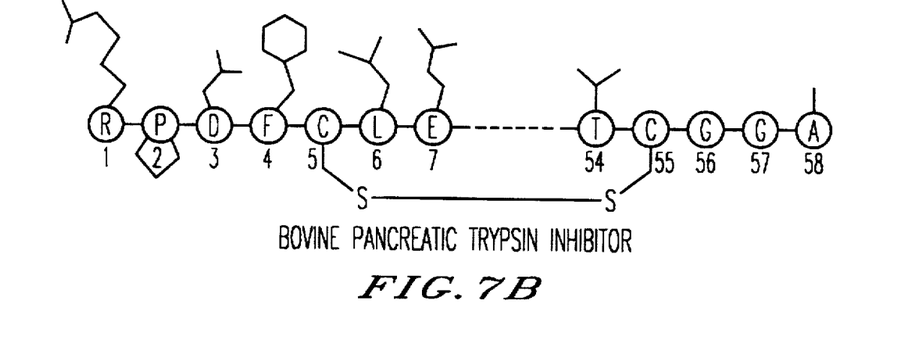

As shown in FIGS. 7A/7B, the side-chain torsion angles of the 38 amino acid residues of the bovine pancreatic trypsin inhibitor are 99 in all, from χ1 of Arg1 to χ1 of Thr 54. Since the number of solution candidates generated are 20 in this embodiment, the prediction computation is applied to 20×99=1980-number of X(L,J,P) from torsion-angle component X(1,1,1) to X(20,54,1).

According to the procedure of the first embodiment described above, 20 initial conformations of side chains of Arg1 are generated arbitrarily or explicitly, candidates having a low degree of van der Waals contact are selected and then processing proceeds to the next step for generating the initial coordinates of side chains of Asp3. By executing "mutation" and "crossover" in this process, new candidates are generated automatically and candidates having a low degree of van der Waals contact are selected.

By way of example, the van der Waals radius can employ a value standardized by the inventors with respect to the crystal structure of protein or peptide (H. Iijima, J. B. Dunbar and G. R. Marshall, 1987, *Proteins: Structure, Function and Genetics*, vol. 2, 330–339) or a 10% contraction value of this value. By changing the contraction ratio, the evaluation of the degree of van der Waals contact can be controlled.

Twenty final candidate conformations where generated in a processing time of 28 minutes by a Silicon Graphics computer in which an R4000/50 MHz chip was installed as the central processing unit. Twenty conformations were obtained. This means that these were conformations in which none of the 99 torsion angles of the side chain were in agreement. In side chains of amino acid residues packed at a high density within the protein in these conformations, the conformations agreed, within a maximum torsion angle of 30°, with conformations determined experimentally by X-ray crystal structure analysis. As for amino acid residues present on the surface, there was a case in which conformations were obtained as solutions though they differed from the conformations found on the basis of crystal structure. In general, it is considered on the basis of experimentation that amino acid residue present on the surface of a protein molecule has a plurality of conformations. This phenomenon does not detract from the effect of the invention. Furthermore, a plurality of conformations of side chains of surface residue thus obtained can be evaluated in terms of appropriateness by applying a solvation energy computation reported by Eisenberg, by way of example.

Thus, according to the present invention as described above, the accuracy obtained is equal to or higher than that of the conventional methods previously reported, and a much higher processing speed is achieved as well. In particular, in comparison with the conventional methods in which only a limited range of conformations can be predicted, the present invention makes it possible to obtain, in a highly precise manner, side-chain conformations observed only rarely in proteins.

Thus, in accordance with the present invention as described in detail above, protein side-chain conformations can be predicted highly accurately in a short period of time.

As many apparently widely different embodiments of the present invention can be made without departing from the spirit and scope thereof, it is to be understood that the invention is not limited to the specific embodiments thereof except as defined in the appended claims.

What is claimed is:

1. A system for predicting protein side-chain conformation having a processor for executing instructions, a storage device for storing data, a random-number generator for generating random numbers, an input unit for entering data and an output unit for outputting data, and provided with a function for predicting side-chain conformation, which is represented by three-dimensional coordinates of atoms constructing the side chain, from a given main-chain conformation of protein, which is represented by three-dimensional coordinates of atoms constructing the main chain of protein, and an amino acid sequence, and a function for analyzing results of prediction, said system comprising:

(a) means for reading the main-chain structure of the protein and an amino acid residue sequence from the storage device in which they have been stored;

(b) means for designating, in a specific order, amino acid residues having the protein side chain to undergo prediction;

(c) means for representing side-chain conformation by side-chain torsion angles and obtaining, from the torsion angles, positions of the atoms constructing the side chains;

(d) means for generating a plurality of solution candidates with regard to side-chain atom positions of a designated amino acid residue;

(e) means for determining, in each side-chain conformation candidate, whether no other atoms are present within the van der Waals radii of each of the protein atoms or, if other atoms are present within the van der Waals radii of each of the protein atoms, determining how close they are;

(f) means for ranking the solution candidates based upon the determination;

(g) means for generating different solution candidates until a solution is obtained in which there are no other atoms present within the van der Waals radii of all protein atoms; and (h) means for writing interim information that prevails during a prediction operation as well as predicted side-chain conformations in said storage device.

2. The system according to claim 1, wherein solution candidates are chosen randomly from a plurality of solution candidates, side chain positions in a chosen solution candidate are randomly selected and random torsion angle values are provided to the chosen solution candidate at the selected side chain positions to mutate the candidate.

3. The system according to claim 1, wherein said means (g) randomly chooses two solution candidates from a plurality of solution candidates, randomly chooses identical side-chain positions in each chosen solution candidate and mutually interchanges torsion angles at the chosen identical side-chain positions of each chosen solution candidate to generate two new solution candidates.

4. The system according to claim 1, wherein said means (e) limits side-chain atoms to undergo determination by storing in which lattice of three dimensional space the atom positions of each solution candidate exist, wherein three-dimensional space is subdivided into lattices the distance between which is twice the van der Waals radius of the atom having the maximum van der Waals radius contained among all of the atoms constructing the protein molecule.

5. A method of predicting protein side-chain conformation having a processor for executing instructions, a storage device for storing data, a random-number generator for generating random numbers, an input unit for entering data and an output unit for outputting data, wherein side-chain conformation, which is represented by three-dimensional coordinates of atoms constructing the side chain, is predicted from a given main-chain conformation of protein, which is represented by three-dimensional coordinates of atoms constructing the main chain of protein, and an amino acid sequence, and results of prediction are analyzed, said method comprising:

(a) reading the main-chain structure of the protein and an amino acid residue sequence from the storage device in which they have been stored;

(b) designating, in a specific order, amino acid residues protein side chain to undergo prediction;

(c) obtaining, by applying from randomly selected angles, positions of atoms constructing side chain of a designated amino acid residue;

(d) generating a plurality of solution candidates with regard to the side-chain atom positions of a designated amino acid residue;

(e) determining, in each solution candidate, whether no atoms are present within the van der Waals radii of each of the protein atoms or, if other atoms are present within the van der Waals radii of each of the protein atoms, determining how close they are;

(f) ranking the solution candidates based upon the determination;

(g) generating different solution candidates and repeating steps (e) and (f) until a solution candidate is obtained in which there are no other atoms present within the van der Waals radii of all protein atoms; and (h) writing interim information that prevails during a prediction operation as well as predicted side-chain conformations in said storage device.

6. The method according to claim 5, wherein said step (e) includes evaluating, with respect to each atom of the main chain and each side-chain atom, whether the atoms are present within each other's van der Waals radii, the evaluation being performed in accordance with the following arithmetic expression:

$$\text{Evaluated value} = \{\Sigma \text{ overlap } (i,j)^M\}^{1/M} \quad \text{Eq. (1)}$$

$$\text{Overlap } (i,j) = \text{All Atoms}$$

$$0 \qquad r_i + r_j \leq d(i,j)$$

$$(r_i + r_j) - d(i,j) \qquad r_i + r_j > d(i,j)$$

where $r_i$, $r_j$ represent the van der Waals radii of atom i and atom j, respectively, and d(i,j) represents the distance between those tow atoms.

7. The method according to claim 6, wherein said evaluating of step (e) comprises the steps of:

(i) calculating, from values of torsion angles of a solution candidate, three-dimensional coordinates of side-chain atoms in terms of a main chain, and registering these three-dimensional coordinates;

(ii) retrieving, from the registered information and main chain structure read in step (a), atoms whose van der Waals radii overlap, and computing a distance between each pair of atoms (i,j) having overlapping van der Waals radii;

(iii) determining whether there is atomic contact in which the distance between atoms is less than a fixed value and, if the distance is less than the fixed value, deciding immediately that this solution candidate is inappropriate; and (iv) evaluating the solution candidate by obtaining results from the arithmetic expression (1).

8. The method according to claim 7, wherein said fixed-value of step (iii) is 0.5Å.

* * * * *

UNITED STATES PATENT AND TRADEMARK OFFICE
CERTIFICATE OF CORRECTION

| | |
|---|---|
| PATENT NO. : 5,724,252 | Page 1 of 1 |
| DATED : March 3, 1998 | |
| INVENTOR(S) : Hiroshi IIjima, et al. | |

It is certified that error appears in the above-identified patent and that said Letters Patent is hereby corrected as shown below:

Title page,
Insert item [73], It should be:

-- [73] Assignee: Kirin Beer Kabushiki Kaisha --

Signed and Sealed this

Second Day of October, 2001

*Attest:*

*Nicholas P. Godici*

*Attesting Officer*

NICHOLAS P. GODICI
*Acting Director of the United States Patent and Trademark Office*